United States Patent
Gagnon et al.

(10) Patent No.: US 11,826,404 B2
(45) Date of Patent: Nov. 28, 2023

(54) PLASMINOGEN TREATMENT OF CONDITIONS ASSOCIATED WITH PAI-1 OVEREXPRESSION

(71) Applicant: PROMETIC BIOTHERAPEUTICS, INC., Rockville, MD (US)

(72) Inventors: Lyne Gagnon, Laval (CA); Brigitte Grouix, Laval (CA); Pierre Laurin, Ville Mont-Royal (CA)

(73) Assignee: PROMETIC BIOTHERAPEUTICS, INC., Rockville, MD (US)

( * ) Notice: Subject to any disclaimer, the term of this patent is extended or adjusted under 35 U.S.C. 154(b) by 459 days.

(21) Appl. No.: 16/625,335

(22) PCT Filed: Jun. 22, 2018

(86) PCT No.: PCT/IB2018/000655
§ 371 (c)(1),
(2) Date: Dec. 20, 2019

(87) PCT Pub. No.: WO2018/234861
PCT Pub. Date: Dec. 27, 2018

(65) Prior Publication Data
US 2021/0330761 A1    Oct. 28, 2021

Related U.S. Application Data

(60) Provisional application No. 62/523,901, filed on Jun. 23, 2017.

(51) Int. Cl.
*A61K 38/48* (2006.01)
*A61P 11/00* (2006.01)
*A61K 31/4418* (2006.01)

(52) U.S. Cl.
CPC ........ *A61K 38/484* (2013.01); *A61K 31/4418* (2013.01); *A61P 11/00* (2018.01)

(58) Field of Classification Search
CPC ................ A61K 38/484; C12N 9/6435; C12Y 304/21007; G01N 33/49
See application file for complete search history.

(56) References Cited

U.S. PATENT DOCUMENTS 11,154,595 B2 * 10/2021 Li .......................... A61K 38/48
11,207,387 B2 * 12/2021 Li ............................ A61P 9/10
2016/0184411 A1    6/2016 Ny et al.

FOREIGN PATENT DOCUMENTS

| CN | PCT/CN2016/110174 | * | 12/2016 | ............ A61K 38/48 |
| NO | 2017081529 A1 | | 5/2017 | |
| WO | 0136351 A2 | | 5/2001 | |
| WO | WO-0158476 A2 | * | 8/2001 | ............ A61K 31/00 |
| WO | 2017077380 A1 | | 5/2017 | |
| WO | 2018107700 A1 | | 6/2018 | |
| WO | WO-2018107698 A1 | * | 6/2018 | ............ A61K 38/48 |

OTHER PUBLICATIONS

Noble et al. "Pirfenidone for idiopathic pulmonary fibrosis: analysis of pooled data from three multinational phase 3 trials" Eur Respir J 2016; 47: 243-253, available online on Dec. 31, 2015 (Year: 2015).*
Marie-Christine Alessi "PAI-1 and the Metabolic Syndrome" Arterioscler Thromb Vasc Biol. Oct. 2006, pp. 2200-2207 (Year: 2006).*
Asish K. Ghosh "PAI-1 in Tissue Fibrosis" J Cell Physiol. Feb. 2012 ; 227(2): 493-507 (Year: 2012).*
PCT/CN2016/110172, Dec. 15, 2016 37 pages (Year: 2016).*
PCT/CN2016/110174, Dec. 15, 2016 63 pages (Year: 2016).*
Shapiro, A.D., et al., "Plasminogen replacement therapy for the treatment of children and adults with congenital plasminogen deficiency." Blood, Mar. 22, 2018, 131(12): 1301-1310.

* cited by examiner

*Primary Examiner* — Thane Underdahl
(74) *Attorney, Agent, or Firm* — SALIWANCHIK, LLOYD & EISENSCHENK

(57) ABSTRACT

The present invention concerns the use of plasminogen, a variant thereof, or an analog thereof having a plasminogen activity, for the prevention or treatment of a condition or a disease that is characterized with an increased PAI-1 level. The conditions and diseases that are characterized with an increased PAI-1 level, are regrouped within two categories: the diseases associated with an impaired vascular or tissue remodeling capacity, and the metabolic and hormonal disorders associated with an increased PAI-1 level.

20 Claims, 3 Drawing Sheets

PLASMINOGEN TREATMENT OF CONDITIONS ASSOCIATED WITH PAI-1 OVEREXPRESSION

CROSS REFERENCE TO RELATED APPLICATIONS

This application is a National Stage Application of International Application Number PCT/IB2018/000655, filed Jun. 22, 2018; which claims the benefit of U.S. Provisional Application No. 62/523,901, filed Jun. 23, 2017, both of which are incorporated herein by reference in their entireties.

FIELD OF INVENTION

The present invention relates to the field of medicine. Particular aspects of the invention relates to the uses of plasminogen for preventing, slowing progression and treating a condition or a therapeutic indication where the PAI-1 level is impaired, the related methods of prevention, slowing progression and treatment, and the use of plasminogen as a PAI-1 modulator.

BACKGROUND OF INVENTION

Several conditions and diseases are known to be characterized by a PAI-1 overexpression in the injured tissue or a PAI-1 overexpression in blood. The drugs that are known to reduce plasma levels of PAI-1, include angiotensin converting enzyme (ACE) inhibitors, insulin-sensitizing agents, and the hormones used in hormone-replacement therapy in women.

In tissues where PAI-1 is overproduced, profound effects on vascular and tissue remodeling capacity are noted (Carmeliet et al. 1997, *Inhibitory role of plasminogen activator inhibitor-1 in arterial wound healing and neointima formation: a gene targeting and gene transfer study in mice*. Circulation 96: 3180-3191). Progressive accumulation of extracellular matrix (ECM) in glomeruli and interstitium is almost universally seen in chronic renal disease, regardless of the underlying disease. There is considerable evidence that the decrease in ECM degradation contributes to matrix accumulation, and that ECM degradation is largely controlled by the plasminogen activator/system. Plasmin contributes to ECM degradation directly, by degrading matrix proteins, including fibronectin, laminin, proteoglycan, and type IV collagen, as well as fibrin, and indirectly, by converting inactive matrix metalloproteinases to active forms that degrade collagenous proteins. Among the most widely studied diseases that appears to be influenced by PAI-1 are glomerulosclerosis and tubulointerstitial fibrosis (Eddy 2002, *Plasminogen activator inhibitor-1 and the kidney*. Am. J. Physiol. Renal Physiol. 283: F209-220), pulmonary fibrosis (Olman et al. 1995, *Changes in procoagulant and fibrinolytic gene expression during bleomycin-induced lung injury in the mouse*. J. Clin. Invest. 96(3): 1621-1630), glomerulonephritis (Keeton et al. 1995, *Expression of type 1 plasminogen activator inhibitor in renal tissue in murine lupus nephritis*. Kidney Int. 47(1): 148-157; and Yamamoto and Loskutoff 1997, *The kidneys of mice with autoimmune disease acquire a hypofibrinolytic/procoagulant state that correlates with the development of glomerulonephritis and tissue microthrombosis*. Am. J. Pathol. 151 (3): 725-734), atherosclerosis (Schneiderman et al. 1992, *Increased type 1 plasminogen activator inhibitor gene expression in atherosclerotic human arteries*. Proc. Natl. Acad. Sci. USA 89(15): 6998-7002; and Chomiki et al. 1994, *Plasminogen activator inhibitor-1 expression in human liver and healthy or atherosclerotic vessel walls*. Thromb Haemost. 72(1): 44-53), chronic obstructive pulmonary disease (COPD) (Wang et al. 2016, *Elevated circulating PAI-1 levels are related to lung function decline, systemic inflammation, and small airway obstruction in chronic obstructive pulmonary disease*. Int. J. Chron. Obstruct. Pulmon. Dis. 11: 2369-2376), chronic kidney disease (CKD) (Eddy and Fogo 2006, *Plasminogen activator inhibitor-1 in chronic kidney disease: evidence and mechanisms of action*. J. Am. Soc. Nephrol. 17(11): 2999-3012), membranous nephropathy (Eddy and Fogo 2006), and chronic allograft nephropathy (Eddy and Fogo 2006).

Studies have identified that the extent of fibrosis corresponds with the pattern and extent of PAI-1 expression (Oikawa et al. 1997, *Modulation of plasminogen activator inhibitor-1 in vivo: a new mechanism for the anti-fibrotic effect of renin-angiotensin inhibition*. Kidney Int. 51: 164-172). Therefore, evidences are that affecting the PAI-1 expression will affect fibrosis, including arteriosclerosis, nephrosclerosis, pulmonary fibrosis, myelofibrosis (Vaughan 2011) and other fibrosis. Overexpression of PAI-1 is observed in lung of patients suffering from idiopathic pulmonary fibrosis, and mainly concentrated in the injured tissue or the inflammatory tissue.

Fibrosis is defined as a fibroproliferative or abnormal fibroblast activation-related disease. Deregulation of wound healing leads to hyperactivation of fibroblasts and excessive accumulation of extracellular matrix (ECM) proteins in the wound area, the pathological manifestation of fibrosis. The accumulation of excessive levels of collagen in the ECM depends on two factors: an increased rate of collagen synthesis and/or decreased rate of collagen degradation by cellular proteolytic activities. The urokinase/tissue type plasminogen activator (uPA/tPA) and plasmin play significant roles in the cellular proteolytic degradation of ECM proteins and the maintenance of tissue homeostasis. The activities of uPA/tPA/plasmin and plasmin-dependent MMPs rely mostly on the activity of a potent inhibitor of uPA/tPA, plasminogen activator inhibitor-1 (PAI-1). Under normal physiologic conditions, PAI-1 controls the activities of uPA/tPA/plasmin/MMP proteolytic activities and thus maintains the tissue homeostasis. During wound healing, elevated levels of PAI-1 inhibit uPA/tPA/plasmin and plasmin-dependent MMP activities, and, thus, help expedite wound healing. In contrast to this scenario, under pathologic conditions, excessive PAI-1 contributes to excessive accumulation of collagen and other ECM protein in the wound area, and thus preserves scarring. While the level of PAI-1 is significantly elevated in fibrotic tissues, lack of PAI-1 protects different organs from fibrosis in response to injury-related profibrotic signals. Thus, PAI-1 is implicated in the pathology of fibrosis in different organs including the heart, lung, kidney, liver, and skin (Ghosh and Vaughan, 2012).

In addition to the above-mentioned conditions, impaired PAI-1 level is also associated with metabolic/hormonal disorders such as obesity, polycystic ovarian disease; and other diseases such as amyloidosis (Vaughan 2011), Alzheimer's disease (Oh et al. 2014, *Plasminogen activator inhibitor-1 as an early potential diagnostic marker for Alzheimer's disease*. Exp. Gerontol. 60: 87-91), alopecia (Vaughan 2011), and aging (Vaughan 2011). Probably the most common clinical condition associated with increased plasmatic PAI-1 production is obesity. Analytical studies of the upstream regulatory region of the PAI-1 gene has allowed the identification of relevant transcriptional response sites, including glucocorticoid response element (GRE) that also localizes aldosterone responsiveness (4), a very-low-density lipoprotein (VLDL) response site (Eriksson et al. 1998, *Very-low-densisty lipoprotein response element in the propomter region of the human plasminogen activator inhibitor-1 gene implicated in the impaired fibrinolysis of hypertriglyceridemia*. Arterioscler. Tromb. Vasc. Biol. 18: 20-26), and two Sp1 sites that appear to mediate glucose-glucosamine responsiveness (Chen et al. 1998, *Sp1 sites mediate activation of the plasminogen activator inhibitor-1 promoter by glucose in vascular smooth cells*. J. Biol. Chem. 273: 8225-8231).

There is a need in the field to discover PAI-1 modulators and their use for the treatment of a multitude of therapeutic indications associated to an abnormal PAI-1 level.

Although reporting several diseases that can be related with an increased level of PAI-1, Vaughan 2011 directs future research towards the development of synthetic orally active PAI-1 antagonists. Nonetheless, Vaughan 2011 warns against complete inhibition of PAI-1 as it can cause abnormal bleeding such as intracranial and joint bleeding after mild trauma, delayed surgical bleeding, severe menstrual bleeding, and frequent bruising. Therefore, there is a need for a compound that does not inhibit or antagonize completely PAI-1, but that lower the expression of PA-1 to a normal level.

BRIEF SUMMARY OF THE INVENTION

The inventors have discovered a PAI-1 modulator that down regulates the PAI-1 overexpression without inhibiting PAI-1 completely. The PAI-1 modulator found by the inventors is not synthetic, but completely natural. It is plasminogen. Surprisingly, the inventors have found that the administration of exogenous plasminogen to a subject having a normal endogenous plasmatic plasminogen activity level, has succeeded to down regulate the PAI-1 expression in injured tissues where PAI-1 was overexpressed. It has been found that the administration of exogeneous plasminogen has repressed the overexpression of PAI-1 in the lung of a subject suffering from idiopathic pulmonary fibrosis (IPF) and has allowed degradation of extracellular matrix (ECM).

General aspects of the invention relate to the pharmaceutical use of plasminogen, a variant thereof, or an analog having a plasminogen activity for the prevention, slowing progression or treatment of a condition or a disease that is characterized with an increased PAI-1 level. General aspects of the invention also relate to a method for the prevention, slowing progression or treatment of a condition or a disease that is characterized with an increased PAI-1 level, comprising the administration of plasminogen, a variant thereof, or an analog having a plasminogen activity. General aspects of the invention further relate the use of plasminogen, a variant thereof, or an analog thereof having a plasminogen activity for the preparation of a medicament for the prevention, slowing progression or treatment of a condition or a disease that is characterized with an increased PAI-1 level. The conditions and diseases that are characterized with an increased PAI-1 level, are, without limitation, regrouped within two categories: the diseases associated with an impaired vascular or tissue remodeling capacity, and the metabolic and hormonal disorders associated with an increased PAI-1 level.

The diseases associated with an impaired vascular or tissue remodeling capacity that can be prevented or treated, or the progression of which can be slowed, by the present invention include, without limitation, chronic renal disease, glomerulosclerosis, fibrosis, tubulointerstitial fibrosis, lung fibrosis, glomerulonephritis, atherosclerosis, chronic obstructive pulmonary disease (COPD), pulmonary fibrosis, idiopathic pulmonary fibrosis, chronic kidney disease (CKD), membranous nephropathy, or chronic allograft nephropathy.

The metabolic or hormonal disorders associated with an increased PAI-1 level to be prevented or treated, or the progression of which can be slowed, by the present invention include, without limitation, obesity, polycystic ovarian disease, amyloidosis, Alzheimer's disease, alopecia, and aging.

The present invention is concerned with the following items:

1. Use of plasminogen, a variant thereof or an analog thereof, for the preparation of a medicament for preventing, slowing progression of, or treating a disease or a condition in a subject, wherein said disease or condition is associated with an overexpression of PAI-1.
2. Use of item 1, wherein the PAI-1 overexpression occurs in blood or in an injured tissue.
3. Use of item 1 or 2, wherein the subject is a non-plasminogen-deficient subject.
4. Use of any one of items 1 to 3, wherein the subject has a plasmatic plasminogen activity that is greater than 70% of a normal plasminogen activity level.
5. Use of any one of items 1 to 4, wherein said disease or a condition associated with an overexpression of PAI-1 is a disease associated with an impaired vascular or tissue remodeling capacity, or a metabolic or hormonal disorder.
6. Use of item 5, wherein the disease associated with an impaired vascular or tissue remodeling capacity is chronic renal disease, glomerulosclerosis, fibrosis, tubulointerstitial fibrosis, glomerulonephritis, atherosclerosis, chronic obstructive pulmonary disease (COPD), pulmonary fibrosis, chronic kidney disease (CKD), membranous nephropathy, or chronic allograft nephropathy.
7. Use of item 5, wherein the metabolic or hormonal disorder is obesity, polycystic ovarian disease, amyloidosis, Alzheimer's disease, alopecia, or aging.
8. Use of item 5, wherein the disease is a pulmonary fibrosis.
9. Use of item 8, wherein the pulmonary fibrosis is idiopathic pulmonary fibrosis.
10. Use of item 8 or 9, wherein plasminogen, a variant thereof or an analog thereof, is used in combination with an antifibrotic agent.
11. Use of item 10, wherein the antifibrotic agent is pirfenidone.
12. Plasminogen, a variant thereof or an analog thereof, for use in preventing the progression of, or treating, a disease or a condition in a subject, wherein said disease or condition is associated with an overexpression of PAI-1.
13. Method for preventing, slowing progression of, or treating a disease or a condition in a subject, wherein said disease or condition is associated with an overexpression of PAI-1, wherein the method comprises the administration of plasminogen, a variant thereof or an analog thereof to the subject.
14. Use of plasminogen, a variant thereof or an analog thereof, for the preparation of a medicament for down regulating a PAI-1 overexpression in an injured tissue of a subject.

15. Plasminogen, a variant thereof or an analog thereof, for use in down regulating a PAI-1 overexpression in an injured tissue of a subject.

16. Method for down regulating a PAI-1 overexpression in an injured tissue of a subject, comprising the administration of plasminogen, a variant thereof or an analog thereof to the subject.

Further aspects of the invention will be apparent to a person skilled in the art from the following description, claims, and generalizations herein.

DETAILED DESCRIPTION OF THE INVENTION

Figure 1:
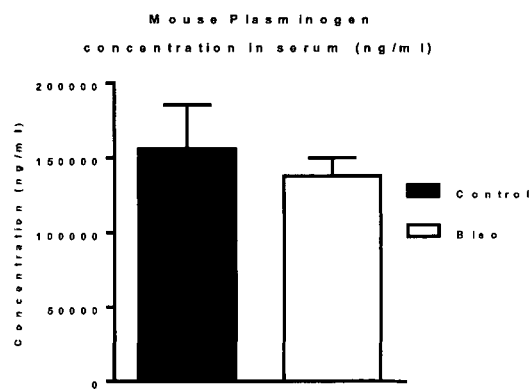
FIG. 1 shows the plasmatic concentration of the endogenous murine plasminogen in bleomycin-induced mice (Bleo) and non-injured mice (Control).

The present discloses the use of a medicament containing plasminogen, a variant thereof, or an analog thereof, for down regulating the PAI-1 overexpression in tissues or in plasma and preferably when the PAI-1 overexpression is associated with a disease or a condition. The present discloses the use of plasminogen, a variant thereof, or an analog thereof, for the prevention, slowing progression or treatment of a disease or condition that is associated with PAI-1 overexpression in tissue or plasma.

The source of plasminogen is variable, and can include, without limitation, purification from blood, plasma or fractions thereof; synthetic production; or recombinant preparation. Variants include, without limitation, amino acids substitution(s), truncations or elongations. Plasminogen include Glu-plasminogen and Lys-plasminogen. Plasminogen can be found in the form of its complete length (1-791), called Glu-plasminogen; or in a shorter version (78-791) called Lys-plasminogen. The variant of plasminogen and the analog of plasminogen that are designated by the present invention include those who have a plasminogen activity.

A PAI-1 overexpression is synonym to an increased PAI-1 level or a PAI-1 level that is above a normal PAI-1 level or an overexpressed PAI-1 level. Said PAI-1 level refers to the PAI-1 level that is either found in plasma or in a tissue of the subject and preferably an injured tissue. The reference range of PAI-1 in blood is 2-15 AU/mL. Increased PAI-1 activity is observed in elderly individuals. The normal plasma concentration is 5-40 ng/mL and mean PAI-1 levels of 50-60 ng/mL are not uncommon in middle-aged male subjects. There is a well-recognized circadian variation in plasma PAI-1, and this fluctuation in PAI-1 activity is responsible for the diurnal variation in net fibrinolytic activity. PAI-1 levels peak in the early morning and correspond with a nadir in net fibrinolytic activity, while the afternoon fall in plasma PAI-1 correspond with a peak in endogenous fibrinolysis. (Vaughan 2005, PAI-1 and atherothrombosis. J. of Thrombosis and Haemostasis, 3: 1879-1883). In an embodiment, a blood PAI-1 overexpression (or PAI-1 overexpressed level) corresponds to a level that is at least 25%, 50%, 100% or 200% above the normal level known for the type of subject (elderly subject, middle-aged male subject, etc.). In an embodiment, a blood PAI-1 overexpression corresponds to a level above 50 ng of PAI-1/mL of blood. In an embodiment, a blood PAI-1 overexpression corresponds to a level above 70 ng of PAI-1/mL of blood. In an embodiment, a blood PAI-1 overexpression corresponds to a level above 100 ng of PAI-1/mL of blood. In an embodiment, a blood PAI-1 overexpression corresponds to a level above 150 ng of PAI-1/mL of blood. In an embodiment, a blood PAI-1 overexpression corresponds to a level above 200 ng of PAI-1/mL of blood. In a subject suffering from arteriosclerosis, tissue PAI-1 levels per 100 mg of tissue have been detected at 99±58 ng in 11 atherosclerotic aortas and 38±20 ng in 5 normal aortas (p<0.05) (Shireman et al. 1996, *Elevated levels of plasminogen-activator inhibitor type 1 in atherosclerotic aorta*. J. of Vasc. Surg., 23:5, 810-818). In an embodiment, a tissue PAI-1 overexpression corresponds to a level above 50 ng of PAI-1 per 100 mg of tissue. In an embodiment, a tissue PAI-1 overexpression corresponds to a level above 70 ng of PAI-1 per 100 mg of tissue. In an embodiment, a tissue PAI-1 overexpression corresponds to a level above 100 ng of PAI-1 per 100 mg of tissue. In an embodiment, a tissue PAI-1 overexpression corresponds to a level above 150 ng of PAI-1 per 100 mg of tissue. In an embodiment, a tissue PAI-1 overexpression corresponds to a level above 200 ng of PAI-1 per 100 mg of tissue.

In an embodiment, the present invention excludes the prevention or treatment of a subject that is plasminogen-deficient; or that has a low plasmatic plasminogen activity level; or that has a plasmatic plasminogen activity level that is lower than the level of plasmatic plasminogen activity in a non-plasminogen-deficient normal subject (called 'normal plasminogen activity'). In other words, the present invention is concerned with the prevention, slowing progression or treatment of a non-plasminogen-deficient subject. The non-plasminogen-deficient subject can be designated as a subject having a normal plasmatic plasminogen level, or a normal subject. Since there is variability in the plasminogen activity of a normal subject, the normal plasminogen activity is preferably calculated in a pool of plasma collected from non-plasminogen-deficient normal subjects or healthy subjects. Said pool of plasma is preferably collected from a sufficiently large amount of subjects so as to normalize the variation found in individuals. Preferably, said pool of plasma is collected from at least 240 non-plasminogen-deficient normal subjects, e.g. 120 healthy male adults and 120 healthy female adults covering ages between 20 and 80 years. In another embodiment, the normal plasminogen activity corresponds to the mean or average plasminogen activity determined in a population of healthy or non-plasminogen-deficient subjects. Several methods to measure the plasminogen activity are known in the art. For example, plasminogen activity is commonly determined by chromogenic or fluorogenic assays. The pool of subjects for the determination of the normal plasminogen activity as well as the method for measuring the plasminogen activity that are preferably used in accordance with the present invention are described in Criteria for specific measurement of plasminogen (enzymatic; procedure) in human plasma, Electronic Journal Of The International Federation Of Clinical Chemistry And Laboratory Medicine, Vol. 12, No. 3, 2000: www.ifcc.org/ifccfiles/docs/plasminogen.pdf. In an embodiment, a low plasmatic plasminogen activity level corresponds to 70% of the normal plasminogen activity or less, 60% of the normal plasminogen activity or less, 50% of the normal plasminogen activity or less, 40% of the normal plasminogen activity or less, 35% of the normal plasminogen activity or less, or 30% of the normal plasminogen activity or less. Said subject that has a low plasmatic plasminogen activity level, includes subject having a congenital plasminogen-deficiency or an acquired plasminogen-deficiency.

In an embodiment, the present invention excludes the prevention or treatment of subject having a congenital plasminogen-deficiency or an acquired plasminogen-deficiency. In an embodiment, the present invention excludes the prevention or treatment of ligneous conjunctivitis, disseminated intravascular coagulation (DIC), sepsis, leukemia, hyaline membrane disease, liver disease, Argentine hemorrhagic fever, hyperthyroidism, post L-asparaginase therapy, thrombolytic event, surgery, Kawasaki disease, burns and severe burns, heterotopic ossification or myositis ossificans, hyaline membrane disease, Neonatal Respiratory Disease Syndrome (NRDS), sepsis, thrombolytic therapy, stroke, Acute Lung Injury (ALI), Acute Respiratory Distress Syndrome (ARDS), Diabetes (Type: 1, 1.5, 2 and 3), fulminant hepatic failure, Budd-Chiari Syndrome, MicroAngiopathic Hemolytic Anemia (MAHAs), Atypical Hemolytic Uremic Syndrome or for wound healing, in any subject or in a subject having a congenital plasminogen-deficiency, an acquired plasminogen-deficiency, a plasmatic plasminogen activity level lower than normal plasminogen activity level, or a plasmatic plasminogen activity level that corresponds to 70% or less of the normal plasminogen activity level. In an embodiment, the subject is a non-plasminogen-deficient normal subject and has a plasmatic plasminogen activity that is greater than 70% of the normal plasminogen activity level.

The term "subject" includes living organisms in need of a treatment as disclosed herein, for example in which an organ is injured. The term "subject" includes animals such as mammals or birds. Preferably, the subject is a mammal, including but not limited to human, horse, dog and cat. In some embodiments, the mammal is not a mouse. More preferably, the subject is a human.

In an embodiment of the invention, plasminogen is administered by one of the following routes of administration: intravenous, intraperitoneal, subcutaneous, nasal, pulmonary, or rectal. In an embodiment, plasminogen is administered subcutaneously by means of a device adapted for slow release delivery, continuous delivery, multiple delivery or a single delivery; or by means of injection with a syringe. In an embodiment, plasminogen is administered intravenously by means of a device adapted for slow infusion, bolus, single or multiple delivery.

The plasminogen can be administered once, or it can be administered with repeated doses. Said repeated doses are preferably administered at the following frequencies: daily, every-other-day, twice-a-week, or weekly. It may be desirable to opt for a high frequency of administrations at the beginning of the treatment so as to reach the desired level quickly and then reduced the frequency of administrations to a desired rate. In another embodiment, the frequency of administration may be decreased after a certain period when some clinical benefits are achieved. Oppositely, in other embodiment, the frequency of administration may be increased after a certain period when some of the desired clinical benefits are not achieved.

In an embodiment, the therapeutically effective dose is between about 0.5 and 20 mg/kg; or 0.5 to 15 mg/kg; or 0.5 to 10 mg/kg; or 2 to 10 mg/kg; or 3 to 10 mg/kg; or 3 to 8 mg/kg; or 4 to 8 mg/kg; or 5 to 8 mg/kg; or 6 to 7 mg/kg; or about 2.0 mg/kg; or about 2.5 mg/kg; or about 3.0 mg/kg; or about 3.5 mg/kg; or about 4.0 mg/kg; or about 4.5 mg/kg; or about 5.0 mg/kg; or about 5.5 mg/kg; or about 6.0 mg/kg; or about 6.5 mg/kg, or about 6.6 mg/kg; or about 7.0 mg/kg; or about 7.5 mg/kg; or about 8.0 mg/kg; or about 8.5 mg/kg; or about 9.0 mg/kg; or about 9.5 mg/kg; or about 10.0 mg/kg. Multiple doses may be suitable to maintain a plasmatic plasminogen level during a desired period of time. The desired period of time varies and can be determined on the basis of the observed symptoms reduction, the achievement of the treatment of a disorder or condition associated with PAI-1 overexpression, or the build up of an efficient plasmatic plasminogen level in prevention of a condition or disorder that is associated with PAI-1 overexpression. The repeated dose can be administered daily, every-other-day, every-two-days, twice-a-week, weekly, or every two-weeks, preferably between daily and weekly. In an embodiment, the dose is administered daily and is between about 0.5 to about 5 mg/kg, or about 3 to about 4 mg/kg, or about 6 to about 7 mg/kg, or about 3.5 mg/kg, or about 5 mg/kg, or about 6 mg/kg, or about 6.6 mg/kg. In an embodiment, the dose is administered every-other-day and is between about 3 to about 7 mg/kg, or about 6 to about 7 mg/kg, or about 4 to about 6 mg/kg, or about 5 mg/kg, or about 6 mg/kg, or about 6.6 mg/kg. In an embodiment, the dose is administered twice-a-week and is between about 4 to about 8 mg/kg, or about 5 to about 7 mg/kg, or about 6 to about 7 mg/kg, or about 6 mg/kg, or about 6.6 mg/kg. In an embodiment, the dose is administered weekly and is between about 5 to about 10 mg/kg, or about 6.5 to about 8.5 mg/kg, or about 6 to about 7 mg/kg, or about 6 mg/kg, or about 6.6 mg/kg, or about 7.5 mg/kg.

In an embodiment, it is desirable that the level of the peaks of plasminogen activity is not higher than about 5 times the normal plasminogen activity (about 500%), about 3 times the normal plasminogen activity (about 300%), about 2.5 times the normal plasminogen activity (about 250%), about 2 times the normal plasminogen activity (about 200%), about 1.75 time the normal plasminogen activity (about 175%), about 1.5 time the normal plasminogen activity (about 150%), about 1.25 time the normal plasminogen activity (about 125%), or about 1 time the normal plasminogen activity (about 100%).

As used herein, the term "therapeutically effective amount" means the amount of compound that, when administered to a subject for treating, slowing progression or preventing a particular disorder, disease or condition associated with impaired PAI-1 levels, or for exerting a biological effect, is sufficient to effect such treatment or prevention of that disorder, disease or condition, or to exert the biological effect. The biological effect designated by the present invention includes the modulation of PAI-1 overexpression in tissue or plasma, the reduction of fibrotic lesions, and/or the stimulation of ECM degradation in a fibrotic organ. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject, the properties of the compounds (e.g., bioavailability, stability, potency, toxicity, etc.), and the particular disorder(s) the subject is suffering from. In addition, the therapeutically effective amount may depend on the subject's blood parameters (e.g., calcium levels, lipid profile, insulin levels, glycemia, coagulation factors, fibrinolytic factors), the severity of the disease state, organ function, or underlying disease or complications. Such appropriate doses may be determined using any available assays including the assays described herein. When plasminogen is to be administered to humans, a physician may for example, prescribe a relatively low dose at first, subsequently increasing the dose until an appropriate response is obtained. The dose to be administered will ultimately be at the discretion of the health care professional. In general, however, it is envisioned that the dose of plasminogen and its frequency of administration may be in the ranges given above for the therapeutically effective dose.

In an embodiment of the present invention, plasminogen is not radiolabelled. In an embodiment of the present invention, plasminogen is comprised in a pharmaceutical composition which is free or substantially free of an additional protein i.e., protein other than plasminogen, and preferably free or substantially free of albumin. In an embodiment of the present invention, plasminogen is comprised in a pharmaceutical composition which is free or substantially free of aprotinin. In an embodiment of the present invention, plasminogen is comprised in a pharmaceutical composition which is substantially free of a trypsin inhibitor. In an embodiment of the present invention, plasminogen is comprised in a pharmaceutical composition which is free or substantially free of a serine protease inhibitor. In an embodiment of the present invention, plasminogen is comprised in a pharmaceutical composition which is free or substantially free of plasmin. In an embodiment of the present invention, plasminogen is comprised in a pharmaceutical composition which is free or substantially free of a surfactant, for instance, a concentration of surfactant that is less than 0.01 mM. The term "substantially free" is intended to mean that the content thereof is below the detection level or below the quantification level.

As used herein, the term "pharmaceutical composition" refers to a preparation of plasminogen that is ready for commercialisation or ready for administration. A pharmaceutical composition may contain at least one pharmaceutically acceptable carrier, diluent, vehicle or excipient. As used herein, the term "pharmaceutically acceptable carrier", "pharmaceutically acceptable diluent" or "pharmaceutically acceptable excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, encapsulating agent, liposome, cyclodextrins, encapsulating polymeric delivery systems and/or polyethyleneglycol matrix, which are acceptable for use in a subject, and preferably acceptable for use in human. The term "acceptable for use" preferably refers to a compound that is approved or approvable by a regulatory agency of the Federal government or State government or listed in the U.S. Pharmacopoeia or other generally recognized pharmacopoeia. The pharmaceutically acceptable vehicle can be a solvent or dispersion medium containing, for example, water, ethanol, polyol (for example, glycerol, propylene glycol, and liquid polyethylene glycol), suitable mixtures thereof, and/or vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin. The nature and the concentration of the pharmaceutically acceptable excipient(s) is(are) chosen so as to provide an acceptable protein stability, ionic strength and pH.

The term "about" herein is intended to define preferably ±5% of the related value, ±10% of the related value, or ±15% of the related value.

EXAMPLES

The following examples further illustrate the practice of this invention but are not intended to be limiting thereof.

Example 1: Plasminogen Preparation

Plasminogen is purified from pooled human plasma that is sourced from FDA/EMA-licensed US plasma collection centers. The resulting purity is above 95%. The purified plasminogen is composed of Glu-plasminogen wherein 95% or more of the plasminogen is a monomer form. The Glu-plasminogen was prepared as described previously in PCT publication WO 2006/120423.

Human plasminogen is comprised of approximately 75 milligrams per vial of lyophilized plasminogen. Prior to infusion, the lyophilized powder in a vial is reconstituted with 12.5 mL of water for intravenous injection. The final composition contains sodium citrate, sodium chloride, glycine and sucrose for providing an acceptable protein stability, ionic strength and pH.

Example 2: Effects of Plasminogen in Pulmonary Fibrosis Mouse Model

Pulmonary fibrosis in mice is induced by intratracheal instillation of bleomycin into the mouse. Bleomycin is well-known anticancer drug. First, the bleomycin insult results in an acute inflammation as soon as day 1. Later at about day 10 to day 14, fibrotic events arise and create a chronic fibrotic condition. The bleomycin-induced mice is recognized as an animal model for pulmonary fibrosis. The evaluation of the activity of plasminogen is undertaken by treatment of the mice with plasminogen at appropriate time points. In the present study, plasminogen was administered at day 10 and day 14.

Male C57BL6 mice are administered intratracheal instillation of bleomycin sulphate (0.007 mg/mouse) at day 0. Human plasminogen was administered subcutaneously at day 10 and day 14, at a dose of either 6 mg/kg, 20 mg/kg, or 60 mg/kg. Animals were sacrificed at day 21. Collagen was quantified by histologic analysis using the staining Red sirus staining (Fluorescence) and analysed at a magnification of 400×. Collagen quantification was performed by segmentation with Image Pro Premier software, and using a sample of 20 fields located in the inflammatory lesions of the lungs. The quantity of collagen has been reported for the total surface of the regions containing inflammatory lesions. This method of quantification allows exclusion of the endogenous content of collagen that is normally contained in the tissue. Since the Control mice have no inflammatory lesion, the percentage of collagen contained in the inflammatory lesion is necessarily zero. CTGF, IL-6 and PAI-1 mRNA expressions were quantified by real-time PCR using mouse Taqman® Gene-Expression assay normalized to HPRT1 endogenous control (Student's t-test).

Figure 2:
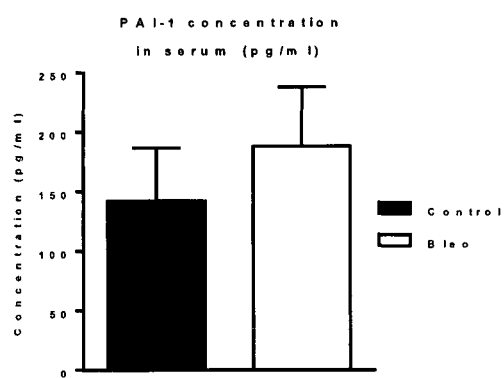
FIG. 2 shows the plasmatic concentration of PAI-1 in bleomycin-induced mice (Bleo) and non-injured mice (Control).
Figure 3:
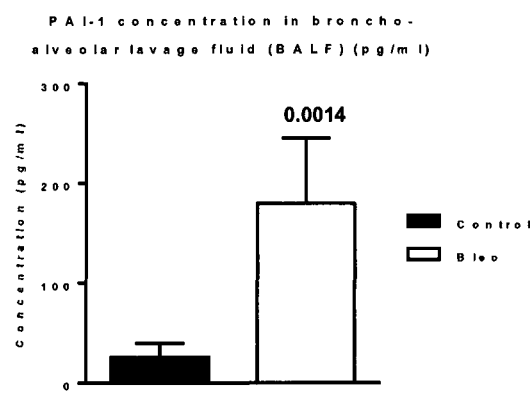
FIG. 3 shows the concentration of PAI-1 in bronchoalveolar lavage fluid (BALF) of bleomycin-induced mice (Bleo) and non-injured mice (Control).

It has been observed that bleomycin has no significant effect on the plasmatic concentration of endogenous murine plasminogen (FIG. 1), and has no significant effect on plasmatic concentration of PAI-1 (FIG. 2). However, bleomycin has significantly increased the concentration of PAI-1 in the broncho-alveolar lavage fluid (BALF) (FIG. 3), which corresponds to the location of the injured tissues as expected by the bleomycin insult.

Figure 4:
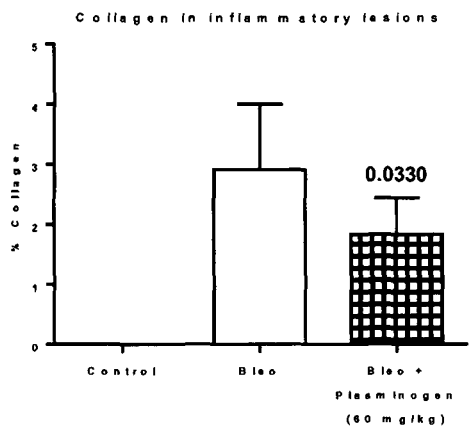
FIG. 4 shows the collagen mRNA expression in inflammatory lesions of (i) normal mouse (Control), (ii) bleomycin-induced mice (Bleo) and (iii) bleomycin-induced mice treated with 60 mg/kg of plasminogen at days 10 and 14 (Bleo+Plg), measured at day 21 following the bleomycin insult.

Collagen expression in the inflammatory lesions have been measured in bleomycin-induced mice that were treated with 60 mg/kg of plasminogen and compared with the bleomycin-induced mice (Bleo) and normal mice (Control). Normal mice (Control) had no inflammatory lesion in the lungs, and therefore, zero percent of collagen has been reported in FIG. 4. Bleomycin-induced mice (Bleo) have presented inflammatory lesions wherein collagen expression is elevated at day 21. This collagen expression is characteristic of the presence of fibrotic lesions in lungs. The amount of collagen expression in the inflammatory lesioins has been significantly reduced by the administrations of 60 mg/kg of plasminogen at day 10 and day 14 in the bleomycin-induced mice (Bleo+Plg).

Figure 5:
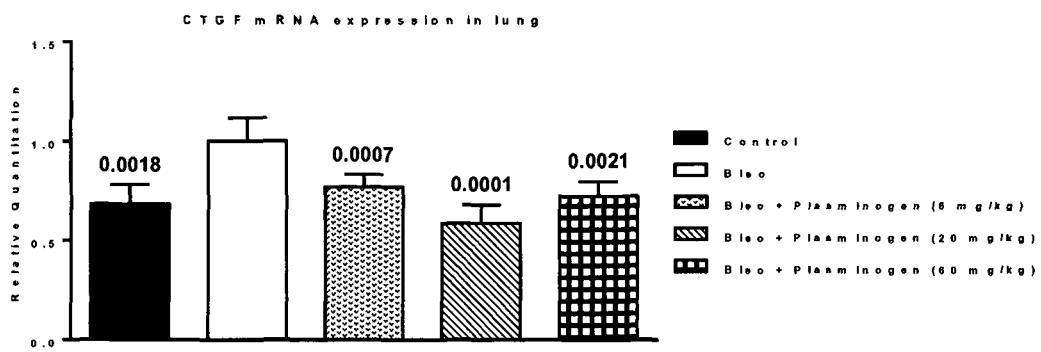
FIG. 5 shows the CTGF mRNA expression in inflammatory lesions of (i) normal mouse (Control), (ii) bleomycin-induced mice (Bleo) and (iii) bleomycin-induced mice treated with 6, 20 or 60 mg/kg of plasminogen at days 10 and 14 (Bleo+Plg) measured at day 21 following the bleomycin insult.

The mRNA expression of CTGF, which is a pro-fibrotic marker, has been measured and reported in FIG. 5. It is shown that the mRNA expression of CTGF in bleomycin-induced mice (Bleo) is increased compared to the CTGF level in normal mice (Control). The administrations of plasminogen at either 6, 20 or 60 mg/kg have significantly reduced the overexpression of CTGF in the bleomycin-induced mice (Bleo+Plg) to a level comparable to the CTGF level of normal mice (Control). The response is not dose-dependent and the variations may result from the small number of studied animals.

Figure 6:
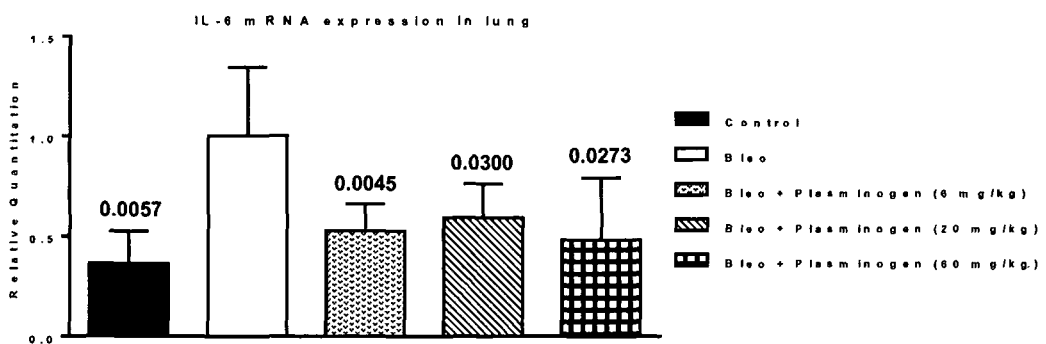
FIG. 6 shows the IL-6 mRNA expression in inflammatory lesions of (i) normal mouse (Control), (ii) bleomycin-induced mice (Bleo) and (iii) bleomycin-induced mice treated with 6, 20 or 60 mg/kg of plasminogen at days 10 and 14 (Bleo+Plg), measured at day 21 following the bleomycin insult.

The mRNA expression of IL-6, which is a pro-fibrotic and pro-inflammatory marker, has been measured and reported in FIG. 6. It is shown that IL-6 is highly overexpressed in bleomycin-induced mice (Bleo) compared to the IL-6 level in normal mice (Control). The administrations of plasminogen at either 6, 20 or 60 mg/kg have significantly reduced the IL-6 mRNA expression in bleomycin-induced mice treated with plasminogen (Bleo+Plg). The response is not dose-dependent and the variations may result from the small number of studied animals.

Figure 7:
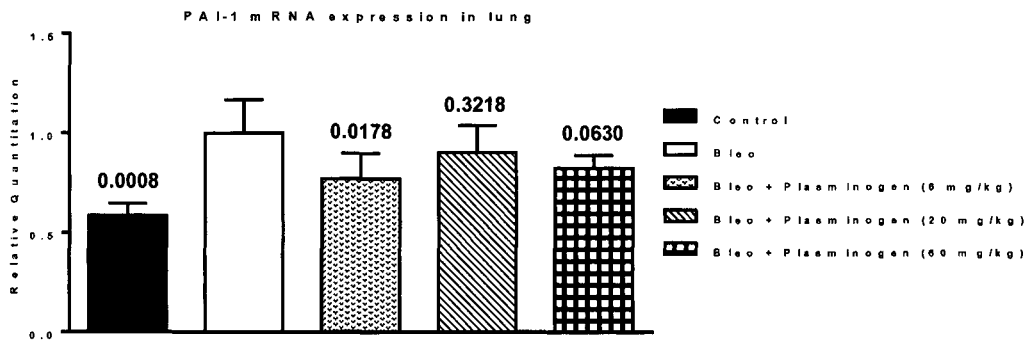
FIG. 7 shows the PAI-1 mRNA expression in inflammatory lesions of (i) normal mouse (Control), (ii) bleomycin-induced mice (Bleo) and (iii) bleomycin-induced mice treated with 6, 20 or 60 mg/kg of plasminogen at days 10 and 14 (Bleo+Plg), measured at day 21 following the bleomycin insult.

The effect of plasminogen on PAI-1 mRNA expression has been reported in FIG. 7. The present study has reaffirmed that that the expression of PAI-1 is increased in injured tissue (lungs) of bleomycin-induced mice (Bleo) compared to the lungs of normal mice (Control), which are not injured. This result corroborates with the PAI-1 level observed in BALF of bleomycin-induced mice (Bleo) that is reported in FIG. 3. The overexpression of PAI-1 in bleomycin-induced mice is reduced by the administrations of plasminogen at all doses (Bleo+Plg). The lack of significant difference between the doses suggests that plasminogen has already reached a maximal effect at the lower dose (6 mg/mkg). These results show that plasminogen down regulates the overexpression of PAI-1, without inhibiting it.

These results indicate that plasminogen has a direct effect on the reduction of lung fibrosis in the bleomycin-induced lung fibrosis model, and may offer the potential as a novel therapy for preventing, slowing the progression of and treating pulmonary fibrosis, including idiopathic pulmonary fibrosis (IPF), and any diseases that are associated with a PAI-1 overexpression. These data also suggest that, in diseases associated with an increased in PAI-1, plasminogen may be efficient in the regulation of PAI-1.

Example 3: Effects of Plasminogen Combined with a Fibrotic Agent in Pulmonary Fibrosis Mouse Model Pulmonary fibrosis in mice is induced by intratracheal instillation of the anticancer drug bleomycin into the mouse. The experiment was performed as described in Example 2, except that murine plasminogen has been administered. Male C57BL6 mice are administered intratracheal instillation of bleomycin sulphate (0.007 mg/mouse) at day 0. Murine plasminogen was administered subcutaneously at days 7, 10, 13, 16 19 and 23, at a dose of 6 mg/kg, alone or in combination with oral administration of 400 mg/kg of pirfenidone (once a day, from day 7 to day 27). Animals were sacrificed on day 28. Collagen was quantified by histologic analysis using the staining Red sirus staining (Fluorescence) and analysed as described in Example 2. IL-6 mRNA expression was quantified by real-time PCR using mouse Taqman® Gene-Expression assay normalized to HPRT1 endogenous control (Student's t-test).

Figure 8:
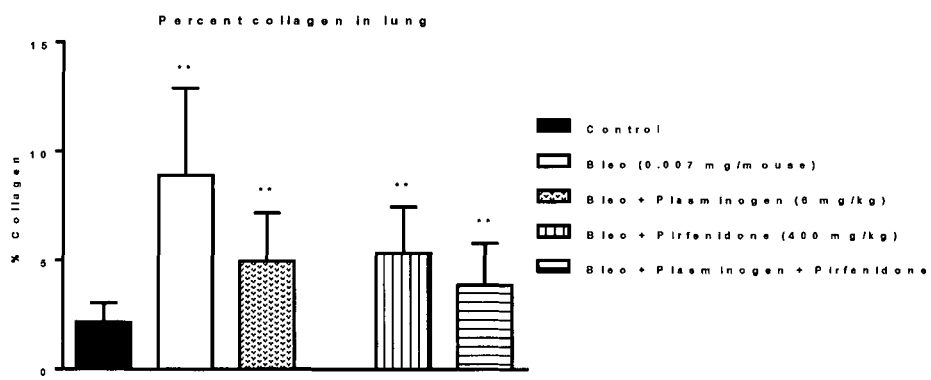
FIG. 8 shows the PAI-1 mRNA expression in inflammatory lesions of (i) normal mouse (Control), (ii) bleomycin-induced mice (Bleo), (iii) bleomycin-induced mice treated with 6 mg/kg of plasminogen (Bleo+Plasminogen), (iv) bleomycin-induced mice treated with 400 mg/kg of pirfenidone (Bleo+Pirfenidone), and (v) bleomycin-induced mice treated with the combinaison of 6 mg/kg of plasminogen and 400 mg/kg of pirfenidone (Bleo+Plasminogen+Pirfenidone), measured at day 28 following the bleomycin insult.

This experiment has tested the combination of plasminogen and pirfenidone, an antifibrotic compound. The results are reported in FIG. 8 where it can be noted that both compounds have been shown to be efficient to reduce fibrosis when administered alone in the bleomycin-induced pulmonary fibrosis mouse model (Bleo+Plasminogen and Bleo+Pirfenidone). Furthermore, FIG. 8 shows that plasminogen combined with pirfenidone (Bleo+Plasminogen+Pirfenidone) have an additive effect on the reduction of collagen expression in the inflammatory lesions of the lungs.

Figure 9:
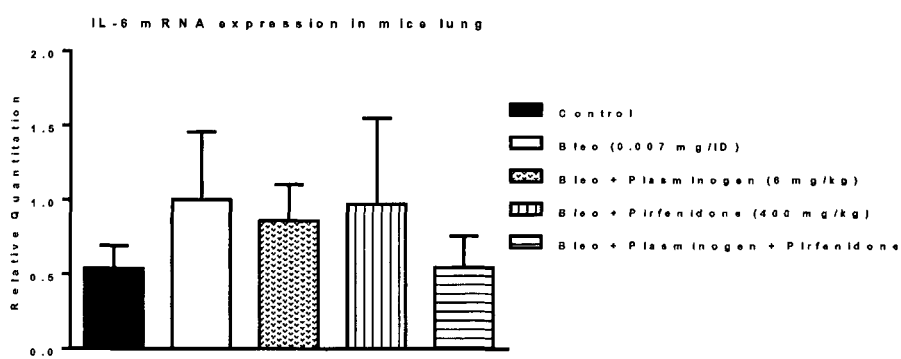
FIG. 9 shows the IL-6 mRNA expression in inflammatory lesions of (i) normal mouse (Control), (ii) bleomycin-induced mice (Bleo), (iii) bleomycin-induced mice treated with 6 mg/kg of plasminogen (Bleo+Plasminogen), (iv) bleomycin-induced mice treated with 400 mg/kg of pirfenidone (Bleo+Pirfenidone), (v) bleomycin-induced mice treated with the combinaison of 6 mg/kg of plasminogen and 400 mg/kg of pirfenidone (Bleo+Plasminogen+Pirfenidone), measured at day 28 following the bleomycin insult.

FIG. 9 has reported that plasminogen inhibits IL-6 mRNA expression (Bleo+Plasminogen). The effect of pirfenidone on IL-6 expression (Bleo+Pirfenidone) was not significantly different than the IL-6 level in non-treated bleomycin-induced mice (Bleo). However, FIG. 9 has demonstrated that the combination of plasminogen and pirfenidone (Bleo+Plasminogen+Pirfenidone) has an additive anti-fibrotic effect, as shown by the significant increased inhibition of IL-6 expression. The IL-6 level in the bleomycin-induced mice treated with the combination of plasminogen and pirfenidone (Bleo+Plasminogen+Pirfenidone) has been lowered to a level comparable to the IL-6 level of normal mice (Control).

Headings are included herein for reference and to aid in locating certain sections These headings are not intended to limit the scope of the concepts described therein, and these concepts may have applicability in other sections throughout the entire specification Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A method for preventing, slowing progression of, or treating, a disease or a condition in a non-plasminogen-deficient subject, wherein said disease or condition is associated with an overexpression of PAI-1, wherein the method comprises:
   a) detecting the PAI-1 level in a blood sample or an injured tissue sample of the subject to determine the overexpression of PAI-1 in the subject, and
   b) administering an effective amount of plasminogen, a variant thereof or an analog thereof to the subject to down-regulate their expression of PAI-1 and prevent, slow the progression of, or treat the disease or condition.

2. The method of claim 1, wherein said disease or a condition associated with an overexpression of PAI-1 is a disease associated with an impaired vascular or tissue remodeling capacity, or a metabolic or hormonal disorder.

3. The method of claim 2, wherein the disease associated with an impaired vascular or tissue remodeling capacity is chronic renal disease, glomerulosclerosis, fibrosis, tubulointerstitial fibrosis, glomerulonephritis, atherosclerosis, chronic obstructive pulmonary disease (COPD), pulmonary fibrosis, chronic kidney disease (CKD), membranous nephropathy, or chronic allograft nephropathy.

4. The method of claim 3, wherein the disease is a pulmonary fibrosis.

5. The method of claim 4, wherein plasminogen, a variant thereof or an analog thereof, is used in combination with an antifibrotic agent.

6. The method of claim 5, wherein the antifibrotic agent is pirfenidone.

7. The method of claim 2, wherein the metabolic or hormonal disorder is obesity, polycystic ovarian disease, amyloidosis, alopecia, or aging.

8. The method of claim 4, wherein the pulmonary fibrosis is idiopathic pulmonary fibrosis.

9. The method of claim 1, wherein the subject has a plasmatic plasminogen activity that is greater than 70% of a normal plasminogen activity level.

10. The method of claim 1, which is used for slowing progression of, or treating, a disease or a condition associated with an overexpression of PAI-1 in a non-plasminogen-deficient subject.

11. The method of claim 1, comprising administering plasminogen to the subject.

12. A method for down-regulating PAI-1 expression in an injured tissue of a subject, wherein said method comprises:
   a) detecting the PAI-1 level in the injured tissue of the subject to determine the overexpression of PAI-1, and
   b) administering an effective amount of plasminogen, a variant thereof or an analog thereof to the subject to down-regulate their expression of PAI-1.

13. The method of claim 12, wherein the subject has a plasmatic plasminogen activity that is greater than 70% of a normal plasminogen activity level.

14. The method of claim 12, comprising administering plasminogen to the subject.

15. A method for slowing progression of or treating pulmonary fibrosis in a subject having pulmonary fibrosis, wherein the method comprises:
   a) detecting a PAI-1 level in a blood sample or injured lung tissue of the subject to determine the overexpression of PAI-1 in the subject, and
   b) administering an effective amount of plasminogen, a variant thereof or an analog thereof to the subject to down-regulate their expression of PAI-1 and prevent, slow the progression of, or treat their pulmonary fibrosis.

16. The method of claim 15, wherein plasminogen, a variant thereof or an analog thereof, is used in combination with an antifibrotic agent.

17. The method of claim 16, wherein the antifibrotic agent is pirfenidone.

18. The method of claim 15, wherein the subject has a plasmatic plasminogen activity that is greater than 70% of a normal plasminogen activity level.

19. The method of claim 15, wherein the pulmonary fibrosis is idiopathic pulmonary fibrosis.

20. The method of claim 15, comprising administering plasminogen to the subject.

* * * * *